(12) United States Patent
Alken et al.

(10) Patent No.: US 6,518,300 B2
(45) Date of Patent: Feb. 11, 2003

(54) TREATMENT OF LIPID METABOLIC DISORDERS USING 5-(1,2-DITHIOLAN-3-YL) VALERIC ACID (α-LIPOIC ACID) OR ITS PHYSIOLOGICALLY COMPATIBLE SALTS

(75) Inventors: Rudolf-Giesbert Alken, Zepernick (DE); Dieter Koegst, Wahlitz (DE); Gerhard Fries, Wahlitz (DE)

(73) Assignees: BiRD Berolina innovative Research and Development GmbH (DE); esparma GmbH (DE)

( * ) Notice: Subject to any disclaimer, the term of this patent is extended or adjusted under 35 U.S.C. 154(b) by 0 days.

(21) Appl. No.: 09/973,152

(22) Filed: Oct. 9, 2001

(65) Prior Publication Data

US 2002/0042444 A1 Apr. 11, 2002

Related U.S. Application Data

(63) Continuation of application No. 09/248,143, filed on Feb. 9, 1999.

(30) Foreign Application Priority Data

Feb. 10, 1998 (DE) .......................................... 198 06 354

(51) Int. Cl.$^7$ .............................................. A61K 31/385
(52) U.S. Cl. ...................................... 514/440; 514/824
(58) Field of Search .................................. 514/440, 824

(56) References Cited

PUBLICATIONS

Sumathi et al. "Impaired lipid metabolism in calcium oxalate stone forming rats and dL –lipoic acid supplementation" 15(1) pp. 59–70. 1995.*

* cited by examiner

Primary Examiner—Theodore J. Criares
Assistant Examiner—Jennifer Kim
(74) Attorney, Agent, or Firm—Kriegsman & Kriegsman

(57) ABSTRACT

Lipid metabolic disorders, such as hyperlipidemia or hyperlipoproteinemia can be treated by administering to an afflicted individual an effective amount of 5-(1,2-dithiolan-3-yl) valeric acid (α-lipoic acid) or one of its physiologically acceptable salts. Pharmaceutical compositions containing (α-lipoic acid) and methods for making such compositions also are disclosed.

1 Claim, No Drawings

TREATMENT OF LIPID METABOLIC DISORDERS USING 5-(1,2-DITHIOLAN-3-YL) VALERIC ACID (α-LIPOIC ACID) OR ITS PHYSIOLOGICALLY COMPATIBLE SALTS

CROSS-REFERENCE TO RELATED APPLICATIONS

The present application is a continuation of U.S. patent application Ser. No. 09/248,143 filed Feb. 9, 1999.

FIELD OF THE INVENTION

The invention concerns the use of 5-(1,2-dithiolan-3-yl) valeric acid (α-lipoic acid) or its physiologically compatible salts for the treatment of disturbances of lipid metabolism.

Arteriosclerosis, after heart disease and cancer, is one of the primary causes of death in humans. A risk factor for the disease of arteriosclerosis is an increased quantity of serum lipids and lipoproteins, so that a decrease in the level of serum lipids and lipoproteins is important for therapy.

An object of the present invention is thus to make available an active ingredient, which is suitable for the treatment of disturbances of lipid metabolism.

SUMMARY OF THE INVENTION

The present invention comprises treating disorders or disturbances in lipid metabolism using 5-(1,2-dithiolan-3-yl) valeric acid (α-lipoic acid) or its physiologically compatible salts. The invention comprises administering to a subject afflicted or thought to be afflicted with a lipid metabolic disorder an effective amount of 5-(1,2-dithiolan-3-yl) valeric acid or a physiologically acceptable salt thereof.

In another aspect, the present invention comprises using 5-(1,2-dithiolan-3-yl) valeric acid (α-lipoic acid) or a physiologically acceptable salt thereof for the production of pharmaceuticals for the treatment of lipid metabolic disorders.

Lipid metabolic disorders which can be treated using the compositions of the invention include, for example, hyperlipidemia and/or hyperlipoproteinemia, particularly hypercholesterolemia and/or hypertriglyceridemia.

It has been found surprisingly that α-lipoic acid is effective for the treatment of disturbances of lipid metabolism. Administration of α-lipoic acid leads to a significant reduction in the blood lipid values both in persons having normal blood lipid values, as well as those having dyslipoproteinemias. These results are independent of whether a simultaneous hypertonia is being treated with medication.

DETAILED DESCRIPTION OF THE INVENTION

α-Lipoic acid was isolated for the first time by Reed et al. (*Science,* 114, p. 93 (1951) and has been used since 1961 as a pharmaceutical for diabetic polyneuropathy and polyneuritis. The production of α-lipoic acid is known in and of itself and is described, for example, in U.S. Pat. No. 2,980,716 and U.S. Pat. No. 3,049,549. α-Lipoic acid has been used for the treatment of polyneuropathy, preferably of diabetic polyneuropathy, in doses of approximately 600 mg/day. The compatibility of oral and parenteral therapy at these doses is very good. In accordance with the present invention, the effective doses for the treatment of disturbances of lipid metabolism are within the same order of magnitude and are thus equally well compatible.

In the present invention, free α-lipoic acid, or a physiologically compatible salt thereof can be used for treatment of a lipid metabolic disorder. Suitable salts can be prepared in ways known in and of themselves from α-lipoic acid with the addition of bases. Suitable bases include, for example, metal hydroxides, particularly alkali and alkaline-earth hydroxides and organic acids, such as, for example, ethylenediamine, trometamol and methylglucamine.

The salts can be obtained by known methods of making pharmaceutical salts, such as, for example, by mixing a free base or a solution thereof with α-lipoic acid or a solution thereof in an organic solvent. Suitable organic solvents include, for example, a lower alcohol such as methanol, ethanol, n-propanol or isopropanol or a lower ketone, such as acetone, methyl ethyl ketone or methyl isobutyl ketone or an ether, such as diethyl ether, tetrahydrofuran, or dioxane. For better separation of the crystals, mixtures of the solvents may also be used. The salts of α-lipoic acid also may be prepared by well-known ion exchange methods.

The subject of the present invention also includes pharmaceuticals for oral, rectal, subcutaneous, intravenous or intramuscular application, which contain α-lipoic acid or its physiologically compatible salts as an active ingredient, in addition to the usual carrier and dilution agents.

The pharmaceuticals of the invention are prepared in the known way with the usual solid or liquid carrier substances or dilution agents and the commonly used technical pharmaceutical adjuvants corresponding to the desired type of application with a suitable dosage. The preferred preparations comprise a form of administration, which is suitable for oral application. Such forms of administration are, for example, tablets, film tablets, sugar-coated pills, capsules, pills, powders, solutions or suspensions or repository forms.

Of course, parenteral preparations, such as injection solutions, are also considered. Further, suppositories will also be named, for example, as forms of preparation.

Corresponding tablets can be obtained, for example, by mixing the active ingredient with known adjuvants, for example, inert dilution agents, such as dextrose, sugar, sorbitol, mannitol, polyvinylpyrrolidone, bursting agents such as corn starch or alginic acid, binding agents such as starches or gelatins, slip additives such as magnesium stearate or talcum and/or agents for obtaining a repository effect, such as carboxy polymethylene, carboxymethylcellulose, cellulose acetate phthalate or polyvinyl acetate. The tablets may also be comprised of several layers.

Appropriately, sugar-coated pills can be prepared by coating analogous cores prepared from tablets with means used commonly in the coating of sugar-coated pills, for example, polyvinylpyrrolidone or shellac, gum Arabic, talcum, titanium dioxide or sugar. Thus, the envelopes for the sugar-coated pills can also comprise several layers, whereby the above-mentioned adjuvants for tablets can be used.

Solvents or suspensions containing the active ingredient according to the invention can also contain agents that improve the taste, such as saccharin, cyclamate or sugar, as well as, for example, flavoring substances such as vanilla or orange extract. They may also contain adjuvants for effecting suspension such as sodium carboxymethylcellulose or preservatives such as p-hydroxybenzoates. Capsules containing active ingredients may be prepared, for example, by mixing the active ingredient with an inert carrier such as lactose or sorbitol and encapsulating in gelatin capsules.

Suitable suppositories can be produced, for example, by mixing with the carrier agents provided for this purpose such as neutral fats or polyethylene glycol or its derivatives.

The following example explains the invention:

EXAMPLE

Within the scope of an open, observational study which did not intervene in the application, 1729 patients with polyneuropathies and simultaneous hypertonia were investigated, who received predominantly a combined therapy of α-lipoic acid and captopril (n=1289). A somewhat smaller group was treated with α-lipoic acid, but not with captopril (n=280). The treatment time extended over approximately 3 months. α-Lipoic acid was predominantly administered orally or parenterally in a dose of 600 mg per day. Captopril was ingested orally in daily doses of 12.5 to 50 mg.

At the beginning of therapy and at the end of observation after three months, the blood lipid values were optionally recorded. In the evaluation of the total population, a statistically striking decrease of triglycerides as well as of the total and LDL cholesterol were shown, along with a slight increase in the HDL cholesterol.

Based on these results from this observation of application, patients who had pathological laboratory values for lipid metabolism were investigated. Because of the different basic treatment, the patients with combined therapy of α-lipoic acid and captopril and those with a single therapy with α-lipoic acid were placed in subgroups for this purpose: the 160 remaining patients (those with single therapy with captopril, n=154; those without treatment data n=6) were not included in the further analysis, since in this remaining group, only a small, incomparable number of patients had initial values corresponding to the range named under point 2 (triglycerides n=0, total cholesterol n=63, HDL cholesterol n=0, LDL cholesterol n=32).

In a first analysis, the parameters were represented independently of one another, i.e., all patients, who had the initial values given below for the parameter, were included for each parameter:

triglycerides >6 mmoles/l;
total cholesterol >6 mmoles/l
HDL cholesterol 0.7–0.8 mmole/l;
LDL cholesterol >2.5 mmoles/l.

The limits of the range were selected based on the studies reported in the literature (H. Thuro, Effective decrease in cholesterol and triglycerides with atorvastatin, Supplement in Der Internist 1996; 37 (8), 1–8).

The data set in the case of triglycerides is represented as follows:

| | | |
|---|---|---|
| Total number of patients with α-lipoic acid therapy: | | 1569 |
| Number of patients with prior or end value: | | 1094 |
| With prior value: 1068, of which: | ≧6 mmoles/l | 37 |
| | <6 mmoles/l | 1031 |
| With end value: 671, of which: | ≧6 mmoles/l | 18 |
| | <6 mmoles/l | 653 |
| with paired data: | | 645 |

Thus a decrease of triglycerides was shown in both therapy groups. Analyzed over all the patients, the mean value was reduced from 8.96 mmoles/l (n=33) to 7.16 mmoles/l (n=26). The reduction of triglycerides over all patients was significant in 26 paired observations (p<0.05). The mean percentual decrease of triglycerides was greater than 20% in all groups.

The data set for total cholesterol was as follows:

| | | |
|---|---|---|
| Total number of patients with α-lipoic acid therapy: | | 1569 |
| Number of patients with prior or end value: | | 1239 |
| With prior value: 1210, of which: | ≧6 mmoles/l | 853 |
| | <6 mmoles/l | 357 |
| With end value: 793, of which: | ≧6 mmoles/l | 490 |
| | <6 mmoles/l | 303 |
| With paired data: | | 764 |

In the total of 853 patients with elevated total cholesterol values prior to therapy (mean value 7.32 mmoles/l), the values decreased to 6.57 mmoles/l, whereby paired values were present in a total of 570 of these patients. In this group, the change was significant (p<0.0001). In the case of a population of 500 patients with paired values in the group with combined therapy and 70 patients in the group with single therapy, the decrease in total cholesterol also showed a high significance (p<0.0001). The mean percent decrease was approximately 10% in all groups.

The data set for HDL cholesterol was as follows:

| | | |
|---|---|---|
| Total number of patients with α-lipoic acid therapy: | | 1569 |
| Number of patients with prior or end value: | | 576 |
| With prior value: 540, of which: | >8 mmoles/l | 28 |
| | ≦8 mmole/l | 512 |
| With end value: 360, of which: | >8 mmoles/l | 12 |
| | ≦8 mmoles/l | 348 |
| With paired data: | | 324 |

In the case of HDL cholesterol, in both groups, a small increase in values was shown. For all the patients, the HDL cholesterol changed on average from 0.76 mmole/l (n=33) to 0.97 mmole/l (n=13). The increase was not significant in either the total group nor in the subgroups (combined therapy n=9, single therapy n=4). The percent increase of the HDL cholesterol was on average over 20%.

The data set for the LDL cholesterol was as follows:

| | | |
|---|---|---|
| Total number of patients with α-lipoic acid therapy: | | 1569 |
| Number of patients with prior or end value: | | 391 |
| With prior value: 369, of which: | ≧2.5 mmoles/l | 336 |
| | <2.5 mmoles/l | 33 |

| -continued | | |
|---|---|---|
| With end value: 251, of which: | ≧2.5 mmoles/l | 226 |
| | <2.5 mmoles/l | 25 |
| With paired data: | | 229 |

In the case of LDL cholesterol, a decrease in the values was shown in both therapy groups. Considered over all the patients, the mean value was reduced from 4.41 mmoles/l (n=336) to 4.03 mmoles/l (n=208). The reduction of LDL cholesterol over all patients was significant in the case of the 208 paired observations (p<0.001). The decrease observed in the subgroups was also significant in the presence of 183 paired values for the combined therapy group and 25 paired values for the single therapy group (combined therapy, p<0.0001, single therapy p<0.001). The percent decrease of the LDL cholesterol was on average approximately 10% in all groups.

In the case of all parameters, the observed changes in the values under therapy were more strongly pronounced in the group of patients with a single therapy of α-lipoic acid in comparison with the group of patients who received a combined therapy with captopril.

In another consideration, the patients were assigned to three groups on the basis of their disease pattern, independent of the form of therapy, according to the "Guidelines of the German Association for Combatting Disorders of Lipid Metabolism and Their Sequelae DGFF (Lipid-Liga) e.V." (Supplement to the German Ärzteblatte 1996; 4, 1–8):

1) isolated LDL-hypercholesterolemia (LDL>4.14, triglycerides≦2.2 mmoles/l);
2) combined LDL-hypercholesterolemia (LDL>4.14, triglycerides>2.2 mmoles/l);
3) isolated hypertriglyceridemia (LDL≦4.14, triglycerides>2.2 mmoles/l).

Standard values from the literature were set as limiting values (Wilson et al., Harrison's Principles of Internal Medicine, 12Edition, McGraw-Hill, 1991).

Sixty-two patients were placed in the first group, 112 patients in the second group, and 83 patients in the third group.

The initial data set for triglycerides was as follows:

| Total number of patients with α-lipoic acid therapy: | | 1569 |
|---|---|---|
| Number of patients with prior or end value: | | 1094 |
| With prior value: 1068, of which: | >2.2 mmoles/l | 560 |
| | ≦2.2 mmoles/l | 508 |
| With end value: 671, of which: | >2.2 mmoles/l | 270 |
| | ≦2.2 mmoles/l | 401 |
| With paired data: | | 645 |

The absolute values of the triglycerides in the first group lay on average at 1.69 mmole/l prior to the beginning of therapy and during the course of therapy increased slightly to 1.70 mmole/l (n=38). The increase was not significant. The second group in its absolute values was somewhat higher than those of the third group with isolated hypertriglyceridemia and showed a greater decrease (prior value 3.75 mmoles/l, end value 2.74 mmoles/l. With the presence of 91 paired values, this difference was highly significant statistically both for the absolute values (0.83 mmole/l) as well as the percent value (20%) with a p<0.0001. In the third group, the values were reduced from 3.33 mmoles/l (n=83) by about 16% to 2.69 mmoles/l (p<0.0001, n=67).

The initial data set for total cholesterol was as follows:

| Total number of patients with α-lipoic acid therapy: | | 1569 |
|---|---|---|
| Number of patients with prior or end value: | | 1239 |
| With prior value: 1210, of which: | >6.2 mmoles/l | 764 |
| | ≦6.2 mmoles/l | 446 |
| With end value: 793, of which: | >6.2 mmoles/l | 405 |
| | ≦6.2 mmoles/l | 388 |
| With paired data: | | 764 |

In the case of total cholesterol, the absolute values in the first group with an average initial value of 7.01 mmoles/l (n=62) and an end value of 6.49 mmoles/l (n=40) lay slightly below those for the individual parameter representation of 7.32 and 6.57 mmoles/l; the decrease amounted to 8% compared with 10%. In the second group, prior and end values (7.71 and 6.86 mmoles/l, n=112 and 94) lay somewhat above those of the single-value representation, whereby the decrease here was approximately equal at 10%. The third group clearly had smaller values. The initial value, however, was still pathological at 6.31 mmoles/l (n=83). Under therapy, it decreased by about 5% to 5.88 mmoles/l (n=67), a value below the pathological range.

The initial data set for HDL cholesterol was as follows:

| Total number of patients with α-lipoic acid therapy: | | 1569 |
|---|---|---|
| Number of patients with prior or end value: | | 576 |
| With prior value: 540, of which: | <0.9 mmole/l | 66 |
| | ≧0.9 mmole/l | 474 |
| With end value: 360, of which: | <0.9 mmole/l | 34 |
| | ≧0.9 mmole/l | 326 |
| With paired data: | | 324 |

In all three groups, the absolute values for HDL cholesterol were clearly higher than those of the individual-parameter representation (group 1: prior value 1.29 mmole/l (n=61), end value 1.34 mmole/l (n=34); group 2: prior value 1.15 mmole/l (n=108), end value 1.15 mmole/l (n=77); group 3: 1.19 mmole/l (n=83), end value 1.31 mmole/l (n=59)). Correspondingly, the absolute and percent increases were also clearly lower, whereby the increase in group 2 at 4.5% was only very slight. Group 1 showed an increase of approximately 10%, which was not significant with only 34 paired values. The increase in HDL cholesterol at approximately 15% percent was most strongly pronounced in group 3; here, a statistically significant difference could be detected in the presence of 59 paired values (p<0.01).

The initial data set for LDL cholesterol was as follows:

| Total number of patients with α-lipoic acid therapy: | | 1569 |
|---|---|---|
| Number of patients with prior or end value: | | 391 |
| With prior value: 369, of which: | >4.14 mmoles/l | 179 |
| | ≦4.14 mmoles/l | 190 |
| With end value: 251, of which: | >4.14 mmoles/l | 91 |
| | ≦4.14 mmoles/l | 160 |
| With paired data: | | 229 |

Based on the increased limiting value, the values for LDL cholesterol in group 1 (prior value 5.02 mmoles/l; end value 4.33 mmoles/l, n=33) and group 2 (prior value 5.42 mmoles/l; end value 4.75 mmoles/l, n=74) were higher than in the above representations (initial value 4.41 mmoles/l, end value 4.03 mmoles/l). In both groups, the mean absolute and percent decreases (16%, 14%) of the LDL cholesterol were highly significant with a p<0.0001. The mean initial value of group 3 at 3.29 mmoles/l was found within the normal range. The end value of this group at 3.23 mmole/l (n=59) was also less than the initial value, although in this group, there was no LDL hypercholesterolemia. The change, however, was not significant.

As could be expected, the ratio of LDL to HDL cholesterol lay in the critical range in the groups with an existing LDL hypercholesterolemia (groups 1 and 2), whereby the quotient in the group of patients with mixed hyperlipidemia both before as well as after therapy lay clearly above that of the group with isolated LDL hypercholesterolemia (isolated: prior value 3.89, end value 3.23; mixed: prior value 4.71, end value 4.13). In both groups, a clear decrease was shown in the ratio of LDL to HDL cholesterol in the course of therapy (isolated by 16.97%, mixed by 12.31%), but it remains within the critical range. In the group of patients without LDL cholesterinolemia, the initial value lay in the normal range, but it was also improved by 10.51%.

A comparison of the classification groups for patients with initial dyslipoproteinemia findings before and after therapy shows a decrease in the group with combined hypercholesterolemia in favor of the isolated forms.

What is claimed is:

1. A method for treating combined LDL hypercholesterolemia in which LDL>4.14 mmoles/l and triglycerides>2.2 mmoles/l, said method comprising administering a pharmacologically effective amount of 5-(1,2-dithiolan-3-yl) valeric acid or a physiologically acceptable salt thereof.

* * * * *